United States Patent [19]

Nakano et al.

[11] 4,231,936
[45] Nov. 4, 1980

[54] MITOMYCIN C DERIVATIVES

[75] Inventors: Kinichi Nakano; Chikahiro Urakawa, both of Machida; Ryoji Imai, Shizuoka, all of Japan

[73] Assignee: Kyowa Hakko Kogyo Kabushiki Kaisha, Tokyo, Japan

[21] Appl. No.: 937,376

[22] Filed: Aug. 28, 1978

[30] Foreign Application Priority Data

Aug. 31, 1977 [JP] Japan ................. 52-103542

[51] Int. Cl.³ ..................... A61K 31/40; C07D 487/04
[52] U.S. Cl. ................. 260/326.24; 424/271
[58] Field of Search ................. 260/326.24; 424/274

[56] References Cited

U.S. PATENT DOCUMENTS

| | | | |
|---|---|---|---|
| 3,332,944 | 7/1967 | Cosulich et al. | 260/326.24 |
| 3,514,452 | 5/1970 | Matsui et al. | 260/326.24 |
| 4,021,449 | 5/1977 | Fujimoto et al. | 260/326.24 |

FOREIGN PATENT DOCUMENTS

| | | |
|---|---|---|
| 1071393 | 6/1967 | United Kingdom . |
| 1110036 | 4/1968 | United Kingdom ............... 260/326.24 |

OTHER PUBLICATIONS

Merck Index, 7th Edition, p. 687 (1960).

*Primary Examiner*—Mary C. Lee
*Attorney, Agent, or Firm*—Wolder, Gross & Yavner

[57] ABSTRACT

The present invention provides new derivatives of mitomycin C, represented by the formula:

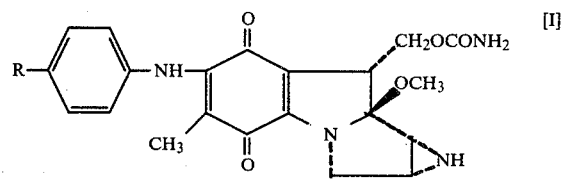

wherein R represents a hydroxy group in which case the composition is designated as 7-N-(p-hydroxyphenyl)-mitomycin C or an amino group in which case it is designated as 7-N-(p-aminophenyl)-mitomycin C. The new compounds are produced by reacting mitomycin A with p-aminophenyl or p-phenylenediamine and exhibit good antitumor and antibacterial activities.

3 Claims, 2 Drawing Figures

MITOMYCIN C DERIVATIVES

SUMMARY OF THE INVENTION

Figure 1:
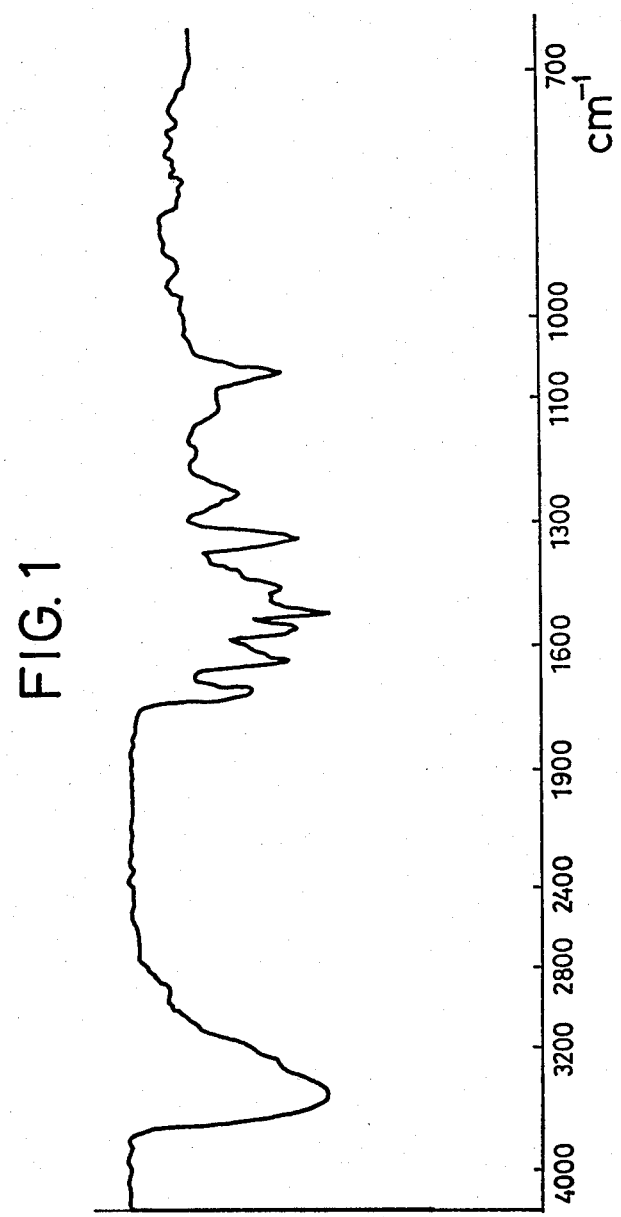
FIGS. 1 and 2 represent the infrared absorption spectrums of 7-N-(p-hydroxyphenyl)-mitomycin C and 7-N-(p-aminophenyl)-mitomycin C, respectively.

The present invention relates to new analogues of mitomycin C, in particular 7-N-substituted mitomycin C and to processess for their preparation. The novel compounds possess interesting physiological activity.

Although mitomycin C possesses interesting antitumor activity it also possesses a relatively high toxicity and as a result it has been desirable to find mitomycin derivatives having lower toxicity. Certain 7a-substituted mitomycin C derivatives have been described in British Patent Specifications Nos. 1,110,036 and 1,071,393 and U.S. Pat. No. 3,332,944 as possessing good antibiotic activity.

The present invention is based upon the discovery that mitomycin C derivatives substituted in the 7a-position of mitomycin C by a p-hydroxyphenyl or p-aminophenyl group possess good antitumor and antibacterial activities and low toxicity. The compounds of the present invention are thus potentially of interest as medicaments.

The compounds of the present invention are represented by the general formula:

[I structure]

wherein R represents a hydroxy group or an amino group. The present invention therefore relates to 7-N-(p-hydroxyphenyl)-mitomycin C and 7-N-(p-aminophenyl)-mitomycin C.

The compounds of the present invention may, for example, be prepared in a manner similar to that described in British Patent Specification No. 1,071,393. Thus, according to a further feature of the present invention there is provided a process for the preparation of compounds of formula I as hereinbefore defined which comprises reacting mitomycin A of the formula:

[II structure]

with p-aminophenol or p-phenylenediamine whereby a compound of formula I as hereinbefore defined is obtained.

The reaction is conveniently conducted in the presence of a solvent, preferably methanol, ethanol or propanol.

The reaction is advantageously carried out using the compound of formula II and the amine in a mol ratio of from 1:100 to 3:1 (preferably from 1:20 to 1:1). The concentration of mitomycin A is conveniently from $10^{-6}$ to 5 mol/liter of solution, preferably from $10^{-3}$ to one mol per liter. The reaction is advantageously effected at a temperature of from $-30°$ to $50°$ C., preferably from $5°$ to $30°$ C. The reaction is generally completed in 3 to 50 hours.

The desired compound may, if desired, be separated from the reaction solution and purified in a conventional manner, such as, for example, by using silica gel column chromatography.

The following Table I shows the minimum inhibitory concentration of the compounds of the present invention. Comparative data similarly obtained by using mitomycin A, mitomycin C and 7-N-phenyl mitomycin C are also shown in this table

TABLE I

| Test microorganism | Test Compound | | | | |
|---|---|---|---|---|---|
| | I | II | III | IV | V |
| Staphylococcus aureus ATCC 6538P | <0.025 | 0.049 | <0.025 | 0.196 | <0.025 |
| Bacillus subtilis ATCC 10707 | <0.025 | <0.025 | <0.025 | 0.049 | <0.025 |
| Shigella sönnei ATCC 9290 | 0.098 | 1.563 | 1.563 | 6.25 | 3.125 |
| Klebsiella pneumoniae ATCC 10031 | <0.025 | <0.025 | 0.098 | 0.391 | 0.049 |

Notes:
I mitomycin A
II mitomycin C
III 7-N-phenyl mitomycin C
IV 7-N-(p-hydroxyphenyl)-mitomycin C
V 7-N-(p-aminophenyl)-mitomycin C The acute toxicity and antitumor activity of the compounds according to the present invention were determined as detailed in the following experiments with the following results. As in Table I compounds III, IV and V denote respectively 7-N-phenyl mitomycin C, 7-N-(p-hydroxyphenyl)-mitomycin C and 7-N-(p-aminophenyl)-mitomycin C.

Compounds III, IV and V have a low solubility in water. The following treatment was performed to make these compounds water-soluble for use in the experiments. A test compound was dissolved in ethanol (about 1000 times by weight) HCO-60, a commercially available surfactant was added in amounts of about 3 times by weight. The mixture was well stirred to dissolve the HCO-60. Ethanol was removed from the solution under reduced pressure by using a rotary evaporator. After this, a test solution was prepared by adding a suitable amount of a physiological saline solution with agitation.

EXAMPLE I: Acute Toxicity Determination

Mice [dd-strain; weight $20\pm1$ g; each group consisted of 5 mice] were used for this experiment. An individual test solution was administered to each mouse by intraperitoneal injection. The test solutions (each 0.5 ml) were prepared by stepwise dilution. After administration of the test solution the mice were observed for 14 days to obtain the mortality of individual mice, from which the $LD_{50}$ values were calculated by Behrens-Karber method. The results are shown in Table 2.

TABLE 2

| Compound No. | $LD_{50}$(mg/kg) |
|---|---|
| IV | 34 |
| V | 18 |

EXAMPLE II: Antitumor Activity

Seven-day-old leukemia cells obtained from the ascites of DBA/2 mice inoculated intraperitoneally with $10^6$ P-388 cells were used. A cell suspension containing $5 \times 10^6$ cells per ml was prepared by using a sterilized physiological saline solution. The test mice ($CDF_1$ mice, 20–25 g) were inoculated with 0.2 ml of the cell suspension containing $1 \times 10^6$ cells intraperitoneally. After 24 hours, the mice were divided into groups (each group consisting of 5 mice) and the test solutions were administered intraperitoneally once only. Survival days were observed for 60 days. In order to evaluate the effects of the test samples, the average survival days were calculated 30 and 60 days after tumor implantation and compared with those of the control group (untreated group). Antitumor activities of the test compounds are indicated by ILS % (increase in life span%) on the basis of the control group.

TABLE 3

| Determined after | | 30 days | | | 60 days | | |
|---|---|---|---|---|---|---|---|
| A | B | C | D | E | C | D | E |
| Con | — | 9.8 ± 0.4 | — | 0/5 | 9.8 ± 0.4 | — | 0/5 |
| IV | 30 | 15.4 ± 0.4 | 57 | 1/5 | 21.4 ±20.7 | 118 | 1/5 |
|  | 20 | 28.4 ± 3.2 | 190 | 4/5 | 47.6 ± 15.8 | 386 | 3/5 |
|  | 10 | 23.0 ± 4.5 | 135 | 1/5 | 23.4 ± 5.1 | 136 | 0/5 |
|  | 5 | 20.4 ± 5.2 | 108 | 1/5 | 20.4 ± 5.2 | 108 | 0/5 |
| V | 20 | 18.4 ± 6.1 | 88 | 1/5 | 24.4 ± 17.9 | 149 | 1/5 |
|  | 15 | 21.6 ± 6.4 | 120 | 1/5 | 21.8 ± 6.7 | 122 | 0/5 |
|  | 10 | 24.6 ± 2.9 | 151 | 1/5 | 26.4 ± 6.4 | 169 | 0/5 |
|  | 5 | 20.0 ± 3.0 | 104 | 0/5 | 20.0 ± 3.0 | 104 | 0/5 |
| III | 20 | 21.6 ± 4.4 | 120 | 1/5 | 21.8 ± 4.8 | 122 | 0/5 |
|  | 15 | 21.2 ± 2.8 | 116 | 0/5 | 21.2 ± 2.8 | 116 | 0/5 |
|  | 10 | 21.8 ± 4.3 | 122 | 1/5 | 22.04 ± 4.6 | 124 | 0/5 |
|  | 5 | 17.84 ± 1.2 | 82 | 0/5 | 17.8 ± 1.2 | 82 | 0/5 |

A-Compoundd No.;
Con - Control;
B- Dose (mg/kg);
C- Average survival days;
D - ILS %;
E - Number of survivors
III = 7-N-phenylmitomycin C
IV = 7-N-(p-hydroxyphenyl) mitomycin C
V = 7-N-(p-aminophenyl) mitomycin C

EXAMPLE III: Antitumor Effect

Mice were inoculated intravenously with P-388 cells ($10^6$/0.2 ml) in a similar manner to that described above in Example II. After 24 hours from inoculation, the test compounds were administered to the mice intravenously once only and the survival effects were observed for 30 days to give the results shown in Table 4. Untreated mice and mice administered with Tween 80 were used for control purpose.

TABLE 4

| A | B | C | ILS % |
|---|---|---|---|
| Con | — | 8.6 ± 0.5 | — |
| Con* | — | 8.6 ± 0.5 | — |
| IV | 30 | 7.6 ± 0.8 | −12 |
|  | 20 | 17.6 ± 4.1 | 105 |
|  | 15 | 16.6 ± 1.5 | 93 |
|  | 10 | 14.0 ± 0 | 63 |
|  | 5 | 11.4 ± 1.4 | 33 |
| V | 30 | 8.4 ± 1.0 | −2 |
|  | 20 | 15.8 ± 5.4 | 84 |
| V | 15 | 23.0 ± 1.7** | 167 |
|  | 10 | 17.8 ± 1.9 | 107 |
|  | 5 | 14.0 ± 0 | 63 |
| III | 30 | 10.0 ± 2.3 | 16 |
|  | 20 | 18.0 ± 1.7** | 109 |
|  | 15 | 15.8 ± 1.5 | 84 |
|  | 10 | 13.6 ± 1.4 | 54 |

TABLE 4-continued

| A | B | C | ILS % |
|---|---|---|---|
|  | 5 | 11.4 ± 1.4 | 33 |

A- Compound No.;
Con- Control (untreated);
Con* -Control administered with 0.5 ml of 1% Tween 80;
B - Dose (mg/kg);
C - Average survival days;
** - P<0.05
III = 7-N-phenyl mitomycin C
IV = 7-N-(p-hydroxyphenyl) mitomycin C
V = 7-N-(p-aminophenyl) mitomycin C

EXAMPLE IV: Effect on Sarcoma-180

Sarcoma 180 cells were inoculated intraperitoneally into dd-strain mice. After 7 days following tumor implantation, ascites tumor cells were obtained from the mice. The cells were washed and a tumor cell suspension containing $5 \times 10^7$ cells per ml was prepared with physiological saline solution. 0.1 ml of the thus-prepared suspension containing $5 \times 10^6$ cells was inoculated into the left inguinal region of each of the test mice (dd-strain; weight 19±1 g; divided into groups, each group consisting of 5 mice). After 24 hours following the inoculation, the test compounds were administered to the mice individually and intraperitoneally. After 4 days following the inoculation, the peripherical blood of the treated mice was obtained by the puncture of the orbital vein. The number of the leucocytes in the peripheral blood was measured by using Toa Microcell Counter CC-108 ( a commercial product of Toa Medical Electronics Co., Ltd., Japan). In order to evaluate the antitumor effects, the tumor was removed 7 days after the inoculation and weighed. Its weight was compared with the average weight of the tumors of the control group (untreated) to give the weight ratios (T/C) shown in Table 5.

TABLE 5

| A | B | T/C | C |
|---|---|---|---|
| Con | — | — | 69.9 ± 16.4 |
| IV | 40 | 0.27 | 40.0 ± 15.3 |
|  | 20 | 0.46 | 39.0 ± 5.6 |
|  | 10 | 0.66 | 64.0 ± 24.6 |
|  | 5 | 0.83 | 63.2 ± 10.2 |
| V | 40 | 0.09 | 13.6 ± 4.6 |
|  | 20 | 0.24 | 24.0 ± 10.2 |
|  | 10 | 0.37 | 34.2 ± 11.2 |
|  | 5 | 0.71 | 58.2 ± 17.1 |
| III | 40 | D* | D* |
|  | 20 | 0.21 | 31.8 ± 11.9 |
|  | 10 | 0.59 | 60.8 ± 18.7 |
|  | 5 | 0.84 | 81.4 ± 21.2 |

A Compound No.
B Dose (mg/kg)
C Average number of leucocyles ($\times 10^2/mm^3$)
Con Control
D* All mice in the group died.

As apparent from these experiments, the compounds of the present invention exhibit good antitumor activity and are potentially of interest as antitumor agents.

In a further feature of the present invention, there are provided pharmaceutical compositions comprising as active ingredient at least one compound of formula I as hereinbefore defined in a pharmaceutically effective amount in association with a pharmaceutical carrier or excipient.

The compositions of the present invention may be presented in a form suitable for oral or parenteral administration.

The compounds according to the present invention have a low solubility in water but may be dissolved in distilled water or glucose to provide an injection solution by subjection, for example, to the treatment for preparation of pharmaceutical compositions described in the following examples. Such pharmaceutical compositions may, for example, be administered intravenously or intraperitoneally once a day, although the amount administered may vary, depending upon the age and symptoms of the patient. A similar amount of active ingredient may also be administered orally. For oral administration the active ingredient is administered in combination with a carrier or excipient, for example, in the form of tablets, powders or granules. For parental administration the active ingredient may, if desired, be administered by intra-arterial, intrathoracic or intraperitoneal injection or by direct injection into the tumor region. For parenteral administration the carrier may be a sterile, parenterally acceptable liquid such as sterile water, sterile glucose solution or a parenterally acceptable oil e.g. arachis oil, contained in ampoules.

For use as an antitumor agent it is advantageous to use from 0.1 to 0.5 mg/kg (body weight) of the active ingredient of the present invention. The active ingredient is conveniently administered once daily, but as stated above the frequency of administration and the amount of active ingredient administered are dependent upon the age and symptoms of the patient to be treated.

Advantageously the compositions may be formulated as dosage units, each unit being adapted to supply a fixed dose of active ingredient. Tablets and ampoules are examples of suitable dosage unit forms. Each dosage unit preferably contains 2 to 60 mg., and especially 5 to 60 mg, of active ingredient.

The following further non-limiting Examples illustrate the production of the mitomycin C derivatives of the present invention:

EXAMPLE 5: 7-N-(p-hydroxyphenyl)-mitomycin C

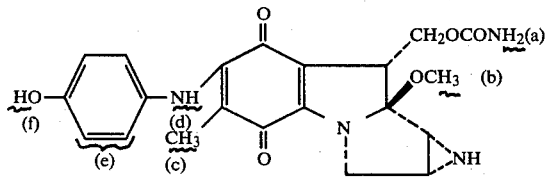

Mitomycin A (1 g) and p-aminophenol (2 g) are added to methanol (100 ml) and the mixture is stirred for 5 hours at room temperature. After completion of the reaction, the reaction solution is concentrated under reduced pressure and then dried in vacuo. The dried product is then subjected to silica gel column chromatography developed by acetone-chloroform mixture (1:1) and recrystallized from an acetone-ether mixture to obtain a desired product (950 mg) in the form of green needle crystals with a yield of 78%. This product shows a green spot (Rf=0.1) by silica gel thin layer chromatography using acetone-chloroform mixture (1:1) as developer. The product does not show a precise melting point.

The chemical shifts (at 60 MHz n.m.r.) of the typical protons of the product are determined using a Varian T-60 nuclear magnetic resonance spectrometer and are indicated by the δ value (ppm) using tetramethylsilane as an internal standard [solvent used for determination: - dimethyl-sulfoxide substituted with deuterium] as follows: (a) 6.47; (b) 3.20; (c) 1.31; (d) 8.40; (e) 6.64–7.03; and (f) 9.35.

The infrared absorption spectrum of the product (using KBr tablet method) is shown in FIG. 1.

Example 6: 7-N-(p-aminophenyl)-mitomycin C

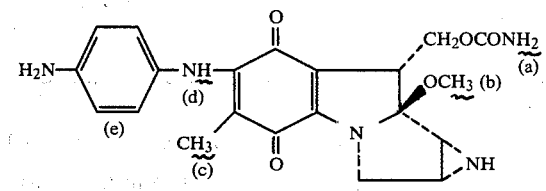

A similar process to that described in Example 5 is carried out with the exception that p-phenylenediamine (2 g) is used instead of p-aminophenol, and the desired product is obtained in the form of green needle crystals (900 mg) in a yield of 74.1%.

Figure 2:
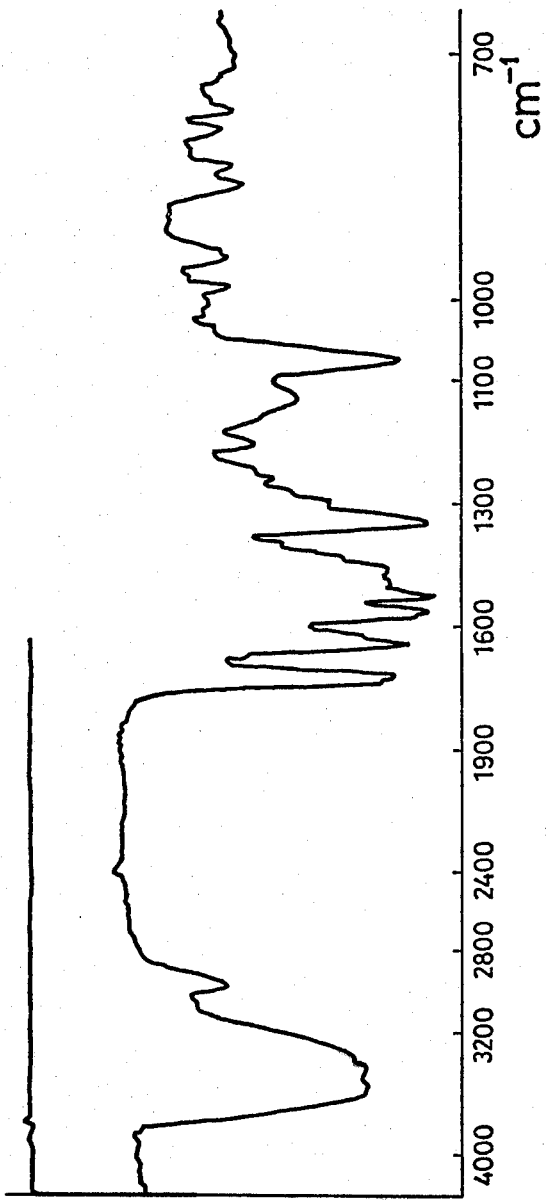

Thin layer chromatography developed using a mixture of acetone and chloroform (1:1) gives a green spot (Rf=0.09), while the product does not show a precise melting point. The chemical shifts (N.M.R. at 60 MHz) of the typical protons of the product are determined and shown by the δ value (ppm) using tetramethylsilane as an internal standard [solvent used:-dimethylsulfoxide substituted with deuterium: CDCl₃ (1:2)] as follows: (a) 6.25; (b) 3.22; (c) 1.36; (d) 8.12; and (e) 6.50–6.90. The infrared absorption spectrum (KBr tablet method) of the product is shown in FIG. 2.

EXAMPLE 7: Preparation of 10,000 Dosages of Injection Solution

7-N-(p-hydroxyphenyl)-mitomycin C (100 g) and HCO-60 (a commercially available surfactant containing polyoxyethylene castor oil ether produced and sold by Nikko Chemicals Co. Ltd., Japan (300 g) were dissolved in ethanol (50 l). The solution was passed through Millipore Membrane Filter (a membrane filter having a pore size of 0.22μ commercially available from Nihon Millipore Ltd., Japan) under pressure for sterilizing. The sterilized filtrate was divided into fractions (each 5 ml) and each fraction was put into a brown vial (capacity 20 ml). Ethanol was removed at 30° C. for 5 hours under reduced pressure of 200 mmHg. The vials were enclosed by rubber stoppers. The thus-obtained vials individually contained 10 mg of 7-N-(p-hydroxyphenyl)-mitomycin C (Compound IV) and 30 mg of HCO-60.

For use, the injection solution is added to a sterilized physiological saline solution (10 ml) and the mixture is shaken well.

EXAMPLE 8: Preparation of 10,000 Enteric Coated Tablets

Compound IV (250 g), lactose (1,100 g) and starch (520 g) are well mixed. The mixed powder is subjected to the convention wet granulation, using a granulating solution (500 ml) consisting of water (500 ml) and polyvinyl alcohol (50 g). The granule is then mixed with magnesium stearate (20 g) and compressed to tablets using a rotary tablet press with 8 mm concaved punches. The tablets of 8 mm in diameter, 4 mm in thickness and 194 mg in weight are obtained. The tablets are coated according to the conventional method using a coating solution having the following composition:

| | |
|---|---|
| Methylene chloride | 1,000 ml |
| Acetone | 1,000 ml |
| Cellulose acetate phthalate | 120 g |
| $SiO_2$ | 10 g |
| $TiO_2$ | 20 g |
| Butylphthalyl butylglycerate | 25 g |

Various modifications of the present invention will occur to those skilled in the art. For example, various known conventional ingredients can be added to pharmaceutical compositions containing the present mitomycin C derivatives.

Having described the present invention that which is sought to be protected is set forth in the following claims.

We claim:

1. A compound of the formula:

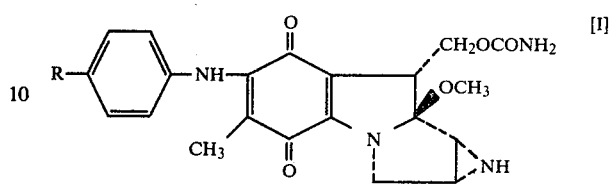

wherein R is selected from the class consisting of a hydroxy group and an amino group.

2. 7-N-(p-hydroxyphenyl)-mitomycin C.
3. 7-N-(p-aminophenyl)-mitomycin C.

* * * * *